July 21, 1959 H. M. TIRET Plant Pat. 1,854
FUCHSIA PLANT
Filed Nov. 28, 1958
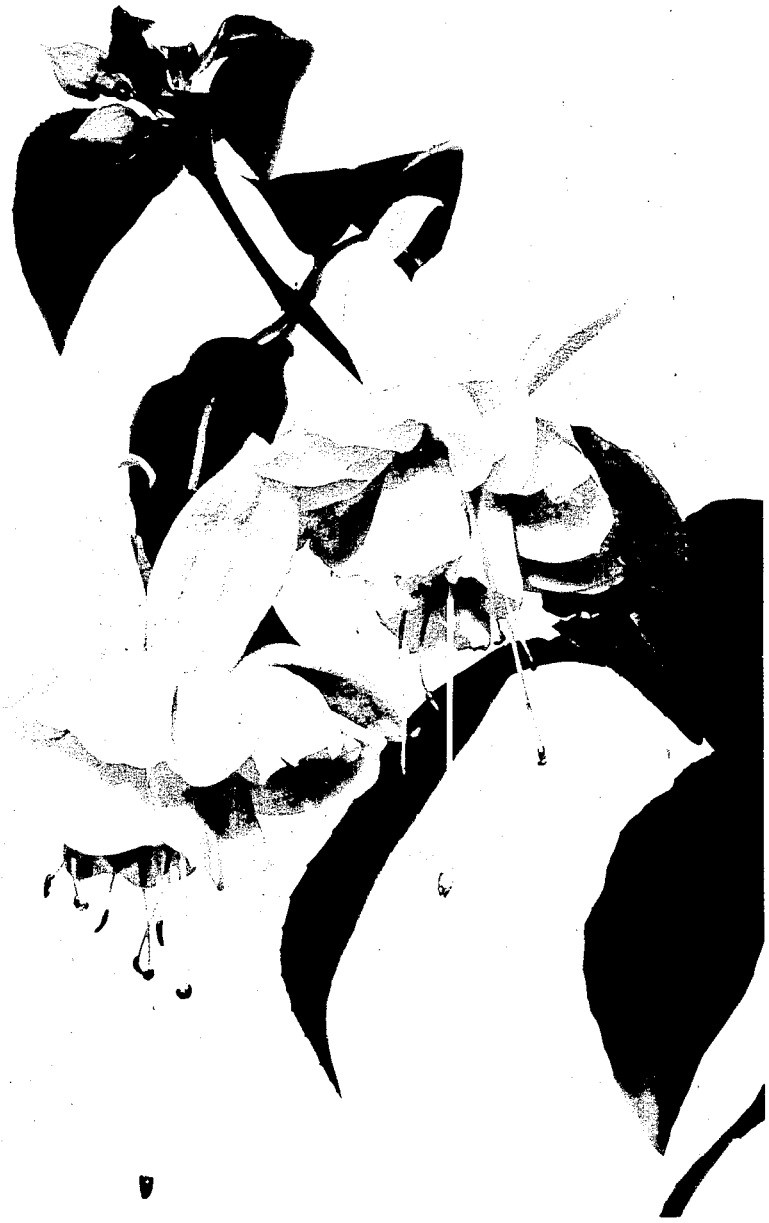

United States Patent Office

Plant Pat. 1,854
Patented July 21, 1959

1,854

FUCHSIA PLANT

Horace M. Tiret, San Francisco, Calif.

Application November 28, 1958, Serial No. 777,163

1 Claim. (Cl. 47—60)

This invention relates to a new and improved fuchsia plant, the principal new and different characteristic of which is the size of the bloom combined with the unusual pink color of the flower.

The accompanying color photograph illustrates the plant in bloom and the new and different characteristics as herein described.

The plant was derived as a hybrid from a seedling (unpatented) not introduced to the trade, namely, 9–43–5, the figures representing applicant's own breeding symbols, and Easter Bonnet (unpatented), not introduced to the trade. The fuchsia plant is distinguished principally by the exceptional pink color of the flower in combination with the extremely large bloom. Specifically, the petals are Rose Pink (British Horticultural Color Chart #427–2), marbled with Carmine (BHCC #21–2), blending and fading evenly throughout as the flower matures. The resulting effect is one not previously existing in any other fuchsia plant. The plant has been asexually reproduced at Colma, California, by cuttings which retained the characteristics of the parent fuchsia plant.

The plant is an upright variety and continuous heavy bloomer and grows vigorously. The leaves are dark green, medium in size, being 2¾″ in length and 1¾″ in width at maturity. They stem from branches which are reddish-brown in color.

In the accompanying drawing, the figure shows a typical branch tip, the drawing representing approximate actual size.

A detailed description of this new variety of fuchsia plant follows:

*Habit of growth.*—Upright variety, quite vigorous, the plant is an early and prolific bloomer.

*Foliage.*—The foliage is a very dark green in color. The branches are reddish-brown. The mature leaf is approximately 2¾″ in length and 1¾″ wide at the widest part. The leaves are veined and crinkly in texture.

*Petals.*—Approximately thirty-two petals occur to each flower, tending from a vertical position in the center to horizontal away from center, creating a flaring form. The diameter of the open, mature flower is approximately 3″, and each of the large petals is approximately 1¼″ by 1¼″ at the widest point. The color of the petals is as described above.

*Ovary.*—Bright green in color, length approximately 5/16″, width at widest point approximately 5/16″, measured at maturity.

*Tube.*—White with greenish cast. The tube is medium short, being approximately ¾″ in length, and ⅜″ in width, at the widest point, measured at maturity.

*Sepals.*—The sepals are four in number, approximately 1¾″ long and ¾″ wide at the widest point, measured at maturity. In form the sepals are broad and fully recurved when the flower is at maturity. The outer side has a smooth and satiny appearance, the underside a crepe-like texture.

*Pistil.*—The style is approximately 3″ in length, and 1/32″ in width, measured at maturity. The style is pale pink in color, and the stigma is a yellow-white.

*Stamens.*—The stamens are eight in number, colored dark rose with rose colored anthers. They are 1¾″ in length, measured at maturity, and medium slender.

*Parentage.*—Applicant's own seedling (unpatented) not introduced to the trade, applicant's breeding symbol 9–43–5 and Easter Bonnet (unpatented).

It is noted that the foliage and flowers will vary somewhat with the seasons and growing conditions; however, the fuchsia plant is thoroughly differentiated from others by reason of the unusual pink color and other characteristics distinctive to it and described and illustrated herein.

Having thus disclosed my discovery, I claim:

The new and distinct variety of fuchsia plant herein described and illustrated characterized by the size of the bloom in conjunction with an unusual attractive pink coloring of the flower.

No references cited.